United States Patent [19]

Bauer et al.

[11] Patent Number: 5,613,985
[45] Date of Patent: Mar. 25, 1997

[54] HAIR COLORING COMPOSITIONS WHICH CONTAIN DEVELOPERS AND PERIMIDINE COUPLERS

[75] Inventors: Wolfgang Bauer, Maintal; Mustafa Akram, Hamburg, both of Germany

[73] Assignee: Hoechst Aktiengesellschaft, Germany

[21] Appl. No.: 532,412

[22] Filed: Sep. 22, 1995

[30] Foreign Application Priority Data

Sep. 24, 1994 [DE] Germany ............... 44 34 165.2

[51] Int. Cl.$^6$ ........................... A61K 7/13
[52] U.S. Cl. .................. 8/409; 8/406; 8/408; 8/423; 8/565; 8/567
[58] Field of Search ................ 8/406, 408, 409, 8/423, 565, 567; 544/249

[56] References Cited

U.S. PATENT DOCUMENTS

| | | | |
|---|---|---|---|
| 1,102,171 | 2/1912 | Schafenberg et al. | 544/249 |
| 4,122,027 | 10/1978 | Cole, Jr. et al. | 252/299 |
| 4,224,326 | 9/1980 | Matsumoto | 544/249 |
| 4,244,071 | 9/1980 | Buell | 106/22 |
| 4,294,964 | 10/1981 | Matsumoto | 544/249 |
| 4,427,802 | 1/1984 | Moulton et al. | 544/249 |
| 4,565,424 | 1/1986 | Huffman et al. | 350/349 |
| 4,599,413 | 7/1986 | Moulton et al. | 544/249 |
| 5,097,029 | 3/1992 | Shannon | 544/249 |
| 5,147,568 | 9/1992 | Luzzi et al. | 544/249 |

FOREIGN PATENT DOCUMENTS

| | | | |
|---|---|---|---|
| 71197 | 2/1983 | European Pat. Off. | 544/249 |
| 2155544 | 3/1973 | Germany. | |
| 59-96171 | 6/1984 | Japan. | |

OTHER PUBLICATIONS

Popp et al., "Synthesis of Potential Anticancer Agents", J. Heterocyclic Chemistry, Abstract. 1964. No month available.

Kuz'menko et al., "Heterocyclic Analogs of Pleiadiene", Khim. Geterotsikl. Soedin., Abstract. 1978. No month available.

*Primary Examiner*—Margaret Einsmann
*Assistant Examiner*—Caroline L. Dusheck
*Attorney, Agent, or Firm*—Connolly & Hutz

[57] ABSTRACT

The present invention relates to the use of a compound of the general formula I

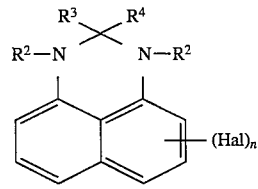

wherein $R^1$ to $R^4$, Hal and n are defined as in claim 1, as a coupler substance for the preparation of oxidation dyestuffs, and to hair colouring compositions which comprise a compound of the general formula I.

12 Claims, No Drawings

HAIR COLORING COMPOSITIONS WHICH CONTAIN DEVELOPERS AND PERIMIDINE COUPLERS

The present invention relates to the use of 2,3-dihydroperimidine derivatives as a coupler substance for the preparation of oxidation dyestuffs, and to hair colouring compositions which comprise a 2,3-dihydroperimidine derivative.

During oxidative dyeing of keratin fibres, dyestuffs or pigments are produced in the fibre by reaction of coupler substances with developer substances in the presence of oxidizing agents.

Numerous use requirements are imposed on such oxidation dyestuffs, in particular in respect of fastness to light, fastness to acid, fastness to perspiration, fastness to rubbing, fastness to permanent waving, fastness to washing, heat stability, fixation capacity, evenness and tinctorial strength. They should also be toxicologically and dermatologically acceptable. They have acquired particular importance because of their high tinctorial strength and good fastness properties in particular (see, for example, J. F. Corbett, in K. Venkataraman, The Chemistry of synthetic Dyes, Vol. V, 478–505 (1971); J. F. Corbett, Rev. Progr. Coloration, Vol. V, 52–58 (1985)).

In practice, coupler and developer substances mixed with suitable auxiliaries are available as hair colouring compositions, from which the dyestuff is then formed in the keratin fibre.

To produce blue colour shades, 1,3-diaminobenzene derivatives are chiefly employed as couplers and 1,4-diaminobenzene derivatives are chiefly employed as developer substances.

Black and black-brown colour shades are obtained from the initially resulting dyestuffs by mixtures with other coupler components, for example with 3-aminophenol and/or 1,3-dihydroxybenzene derivatives.

Surprisingly, it has now been found that in addition to blond colour shades, black to black-brown dyeings can be obtained by a direct route if 2,3-dihydroperimidine derivatives are employed as coupler substances.

The present invention accordingly relates to the use of a compound of the general formula 1

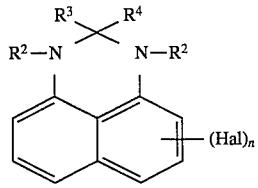

wherein
$R^1$ and $R^2$ independently of one another are hydrogen, $(C_1-C_4)$-alkyl, hydroxy-$(C_1-C_3)$-alkyl, 2,3-dihydroxypropyl, 2-hydroxy-3-$(C_1-C_4)$-alkoxypropyl, phenyl or substituted phenyl,
$R^3$ and $R^4$ independently of one another are hydrogen, trichloromethyl, $(C_1-C_4)$-alkyl, di-$(C_1-C_2)$-alkoxymethyl, hydroxy-$(C_1-C_4)$-alkyl, phenyl or substituted phenyl,
Hal is fluorine, chlorine or bromine and
n is 0, 1 or 2,
as a coupler substance for the preparation of oxidation dyestuffs.

Alkyl groups can be straight-chain or branched and are, for example, methyl, ethyl, isopropyl, n-propyl, n-butyl, isobutyl, sec-butyl, tert-butyl, pentyl or hexyl. Analogous conditions apply to alkoxy groups. Substituted phenyl can carry 1, 2 or 3 identical or different substituents. Suitable substituents are hydroxyl, $(C_1-C_4)$-alkyl, $(C_1-C_4)$-alkoxy, fluorine, chlorine, bromine or else the methylenedioxy radical, which simultaneously replaces two hydrogen atoms of the phenyl radical.

$R^1$ and $R^2$ are preferably, independently of one another, hydrogen, methyl, 1-hydroxyethyl, 2-hydroxyethyl, 2-hydroxypropyl, 3-hydroxypropyl or phenyl.

$R^3$ and $R^4$ are preferably, independently of one another, hydrogen, trichloromethyl, $(C_1-C_6)$-alkyl, hydroxymethyl or substituted phenyl.

Hal is preferably in the 4- and/or 6-position of the perimidine skeleton and is preferably chlorine.

The compounds of the general formula I are preferably incorporated into so-called hair colouring compositions as a mixture with one or more developer substances.

The present invention accordingly also relates to a hair colouring composition comprising a coupler substance and a developer substance, characterized in that it comprises a compound of the general formula I as the coupler substance.

The hair colouring compositions according to the invention comprise the compounds of the general formula I in neutral form or in salt form in an amount sufficient for dyeing, preferably 0.01 to 5% by weight, particularly preferably 0.1 to 3% by weight, based on the total weight of the composition. In addition, the compounds of the general formula I can be employed by themselves or as a mixture with one another.

The hair colouring compositions according to the invention can also comprise other coupler substances or mixtures of other coupler substances, in addition to the compounds of the general formula I, as a rule amounts of 0.01 to 5% by weight, preferably 0.1 to 3% by weight, based on the total weight of the composition, being employed.

Suitable other coupler substances are, for example, 1,3-dihydroxybenzene 2-methyl-1,3-dihydroxybenzene, 2-amino-4-(2'-hydroxyethylamino)-anisole, 2-amino-4-(2'-hydroxyethylamino)-phenetole, 2-amino-4-ethylaminoanisole, 2,4-diaminobenzyl alcohol, 2,4-diamino-phenoxyethanol, 1,3-diaminobenzene, 3-aminophenol, 3-amino-2-methylphenol, 4-amino-2-hydroxyphenoxyethanol, 4-hydroxy-1,2-methyenedioxybenzene, 4-(2'-hydroxyethylamino)-1,2-methylenedioxybenzene, 2,4-diamino-5-ethoxytoluene, 4-hydroxyindole, 5,6-dihydroxyindole, 1-naphthol and 1,5-dihydroxynaphthalene.

The developer substances which the hair colouring compositions according to the invention comprise are preferably present in amounts of 0.01 to 5% by weight, particularly preferably 0.1 to 3% by weight, based on the total weight of the composition. The developer substances can also be employed by themselves or as a mixture with one another.

Suitable developer substances are, for example, 1,4-diaminobenzene, 2,5-diaminotoluene, 2,5-diaminobenzyl alcohol, 4-aminophenol, 4-amino-3-methylphenol, 2,5-diaminopyridine, tetraaminopyrimidine and physiologically tolerated salts thereof.

If appropriate, the hair colouring compositions according to the invention can also comprise other coloured components, and in particular directly absorbing hair dyestuffs and/or anthraquinone dyestuffs and/or azo dyestuffs. Suitable coloured components of the classes of substance mentioned are described, for example, by K. Venkataraman, The Chemistry of Synthetic Dyes, Vol. V, pages 507–529 (1971). The hair colouring compositions according to the invention comprise the other coloured components mentioned in amounts of, for example, 0.01 to 5% by weight, based on the total weight of the composition.

The hair colouring compositions according to the invention are advantageously present in the form of cosmetic formulations, for example, as creams, emulsions or gels, which comprise auxiliaries customary in cosmetics, in addition to the oxidation dyestuff precursors mentioned. Customary auxiliaries are, for example, anionic or nonionic emulsifying agents, thickeners and antioxidants, such as ascorbic acid, thioglycolic acid or sodium sulphite.

The hair colouring compositions according to the invention can be weakly acid, neutral or alkaline, depending on their make-up. They preferably have a pH of 8.0 to 11.5, it being possible for the pH to be established, for example, with ammonia, potassium carbonate, sodium hydroxide or potassium hydroxide.

The hair colouring compositions according to the invention can be prepared in a simple manner by mixing one or more compounds of the general formula I with one or more developer substances and if appropriate other coupler substances, other colour components and/or suitable auxiliaries, and if appropriate establishing the desired pH.

The oxidative dyeing, i.e. the reaction of the coupler and developer substances mentioned, can in principle be carried out with atmospheric oxygen, if appropriate with the addition of catalysts which are known per se. Preferably, however, hydrogen peroxide, for example as a 6% strength aqueous solution, addition products thereof on urea or melamine, sodium perborate, potassium peroxydisulphate or mixtures of the compounds mentioned are employed as oxidizing agents.

In practice, for example, a hair colouring composition according to the invention is mixed with one of the oxidizing agents mentioned shortly before use and the mixture is applied to the hair. The use temperatures vary in the range from 15° to 40° C. After an action time of about 30 minutes, the residual composition is removed from the hair by rinsing and the hair is subsequently washed with a mild shampoo and dried.

The compounds of the general formula I are known in some cases and are described, for example, in Compt. Rend. 252, 899 (1961), Chem. Heterocycl. Compd. 14, 1145 (1978), Chem. Heterocycl. Compd. 14, 1156 (1978), J. Heterocycl. Chem. 5, 591 (1968), Pharm. Chem. J. 12, 899 (1978), Compt. Rend. 224, 1569 (1947) or Chem. Heterocycl. Compd. 10, 484 (1974), but in some cases are also new.

The present invention also relates to compounds of the general formula I, wherein
$R^1$ and $R^2$ are both hydrogen or both hydroxy-$(C_1-C_3)$-alkyl or $R^1$ is $(C_1-C_4)$-alkyl and $R^2$ is hydroxy-$(C_1-C_3)$-alkyl,
$R^3$ and $R^4$ are both hydrogen or both hydroxy-$(C_1-C_3)$-alkyl or $R^3$ is $(C_1-C_4)$-alkyl and $R^4$ is hydroxy-$(C_1-C_3)$-alkyl,
Hal is fluorine, chlorine or bromine and
n is 0, 1 or 2,
wherein $R^1$, $R^2$, $R^3$ and $R^4$ cannot simultaneously be hydrogen, if n=0.

The compounds of the general formula I can be prepared, for example, by reaction of 1,8-diaminonaphthalene derivatives of the general formula II

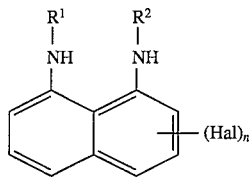

with carbonyl compounds of the general formula III

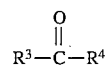

wherein $R^1$ to $R^4$, Hal and n are defined as above (see, for example, Compt. Rend. 252, 899 (1961), Chem. Heterocycl. Compd. 14, 1156 (1978), J. Heterocycl. Chem. 5, 591 (1968), Pharm. Chem. J. 12, 899 (1978), Compt. Rend. 224, 1569 (1947)). Suitable compounds of the general formula II are, for example, 1,8-diaminonaphthalene, 1-methylamino-8-aminonaphthalene, 1-phenylamino-8-amino-naphthalene 2-chloro-1,8-diaminonaphthalene and 1,8-bis-(2-hydroxyethylamino)-naphthalene.

Suitable compounds of the general formula III are, for example, formaldehyde, acetaldehyde, propionaldehyde, butyraldehyde, isobutyraldehyde, acetone, methyl ethyl ketone, diethyl ketone, methyl propyl ketone, ethyl isopropyl ketone, methyl isobutyl ketone, 3-methoxybutyraldehyde, hydroxyacetone, dihydroxyacetone, diacetone alcohol, 1,5-dihydroxy-2-methyl-3-pentanone, glyceraldehyde, glyoxal monodimethyl acetal, glyoxal monodiethyl acetal, benzaldehyde, piperonal, vanillin and salicylaldehyde.

Compounds of the general formula I where n=1 or 2 furthermore can be obtained by reaction of compounds of the general formula I where n=0 with, for example, sulphuryl chloride (Chem. Heterocycl. Compd. 14, 1145 (1978)).

Compounds of the general formula I furthermore can be obtained by reduction Of corresponding perimidine derivatives, 1,3-dialkylperimidinium salts or 1,3-dialkylperimidin-2-ones with lithium aluminium hydride or sodium borohydride (Chem. Heterocycl. Compd. 10, 485 (1974)).

If appropriate, the compounds of the general formula I can be present in the form of acid addition compounds. Hydrochlorides and hydrosulphates are particularly preferred.

The oxidation dyestuffs obtained from the compounds of the general formula I and developer substances which are known per se have outstanding use properties, in particular in respect of fixation, tinctorial strength and covering power, as well as fastness to washing, fastness to acid and heat stability.

As a constituent of the hair colouring compositions according to the invention, the compounds of the general formula I furthermore have excellent storage stability.

The following examples serve to illustrate the subject-matter of the invention without limiting it to the examples mentioned.

EXAMPLE 1

2-Methyl-2-hydroxymethyl-2,3-dihydroperimidine, hydrosulphate

A mixture of 79.1 g of 1,8-diaminonaphthalene, 57.4 g of 96% strength sulphuric acid and 700 ml of water is initially introduced into the reaction vessel at 50° C., and 57.8 g of hydroxy acetone are metered in over a period of 10 minutes. The mixture is then subsequently stirred at 50° C. for 2 hours and cooled to 0° C., and the product is isolated by filtration and dried at 70° C. in vacuo.

Yield: 71.6 g of grey crystalline powder
Melting point: 115°–118° C.

The following can be prepared in an analogous manner:

EXAMPLE 2

1,3-bis-(2-hydroxyethyl)-2,3-dihydroperimidine, hydrosulphate

Melting point: >200° C.

EXAMPLE 3

1,2-bis-hydroxymethyl-2,3-dihydroperimidine, hydrosulphate

Melting point: 150–153° C.

EXAMPLE 4

Hair colouring composition in cream form 1.98 g of 2,2-dimethyl-2,3-dihydroperimidine
1.85 g of p-phenylenediamine·2HCl
1.20 g of oleic acid
0.50 g of sodium dithionite
6.20 g of lauryl alcohol diglycol ether-sulphate, sodium salt (28% strength solution
18.0 g of cetyl-stearyl alcohol
7.50 g of ammonia, 25% strength water to 100

60 g of the hair colouring composition mentioned above are mixed with 60 g of 6% strength hydrogen peroxide solution shortly before use. The mixture is allowed to act on pale brown natural hair with a 40% grey content at 40° C. for 35 minutes. Thereafter, the coloured composition is rinsed out, and the hair is subsequently shampooed and dried. The hair has been given a uniform medium brown shade with a violet character.

EXAMPLE 5

Hair Colouring Composition in Gel Form 1.98 g of 2,2-dimethyl-2,3-dihydroperimidine
0.10 g of p-aminophenol
12.0 g of oleic acid
12.0 g of isopropanol
5.00 g of nonoxynol-4
10.0 g of ammonia, 25% strength
0.5 g of sodium sulphite, anydrous water to 100

50 g of the colouring composition mentioned above are mixed with 75 g of 6% strength hydrogen peroxide solution shortly before use. The mixture is allowed to act on medium-blond natural hair at 35° C. for 30 minutes. Thereafter, the coloured composition is rinsed out, and the hair is subsequently shampooed and dried. The hair has been coloured an intensive dark golden blond.

EXAMPLE 6

Hair Colouring Composition in Cream Form 3.20 g of 2-methyl-2-hydroxymethyl-2,3-dihydroperimidine, hydrosulphate
1.98 g of p-phenylenediamine·2HCl
0.12 g of m-aminophenol
2.00 g of oleic acid
0.10 g of polyacrylic acid
0.50 g of sodium sulphite, anyhydrous
4.00 g of lauryl alcohol diglycol ether-sulphate, sodium salt (28% strength solution)
8.00 g of ammonia, 25% strength water to 100

50 g of the hair colouring composition mentioned above are mixed with 50 g of 6% strength hydrogen peroxide solution shortly before use. The mixture is allowed to act on pale blond natural hair with a 50% grey content at 25° C. for 30 minutes. Thereafter, the coloured composition is rinsed out, and the hair is subsequently shampooed and dried. It has been given an intensive graphite black shade.

EXAMPLE 7

Hair Colouring Composition in Gel Form 3.20 g of 2-methyl-2-hydroxymethyl-2,3-dihydroperimidine, hydrosulphate
2.2 g of 2,5-diaminotoluene sulphate
0.35 g of 3-nitro-4-aminophenol
14.0 g of oleic acid
10.0 g of isopropanol
2.00 g of PEG-3-cocamines
10.0 g of ammonia, 25% strength
0.50 g of ascorbic acid water to 100

40 g of the colouring composition mentioned above are mixed with 60 g of 6% strength hydrogen peroxide solution shortly before use. The mixture is allowed to act on pale blond natural hair at 40° C. for 30 minutes. Thereafter, the coloured composition is rinsed out, and the hair is subsequently shampooed and dried. The hair has been coloured an intensive graphite shade with a slightly reddish reflection.

EXAMPLE 8

Hair Colouring Composition in Cream Form 3.38 g of 2,2-bis-hydroxymethyl-2,3-dihydroperimidine, hydrosulphate
1.20 g of p-aminophenol
0.30 g of m-aminophenol
0.25 g of HC Red No. 3
0.05 g of m-phenylenediamine
2.50 g of lauryl ether-sulphate sodium salt (70% strength paste)
1.00 g of oleic acid
0.60 g of sodium sulphite, anhydrous
12.0 g of cetyl alcohol
6.00 g of myristyl alcohol
1.00 g of propylene glycol
10.0 g of ammonia, 25% strength water to 100

60 g of the colouring composition mentioned above are mixed with 60 g of 6% strength hydrogen peroxide solution shortly before use. The mixture is allowed to act on pale blond natural hair with a 20% grey content at 40° C. for 30 minutes. Thereafter, the coloured composition is rinsed out, and the hair is subsequently shampooed and dried. The hair has been coloured a mocha brown.

EXAMPLE 9

Hair Colouring Composition in Gel Form 3.38 g of 2,2-bis-hydroxymethyl-2,3-dihydroperimidine, hydrosulphate
1.98 g of p-phenylenediamine·2HCl
6.00 g of nonoxynol-4
14.0 g of oleic acid
1.50 g of PEG-3-cocamine
14.0 g of ispropanol
10.0 g of ammonia, 25% strength
0.45 g of sodium sulphite, anhydrous water to 100

40 g of the colouring composition mentioned above are mixed with 60 g of 6% strength hydrogen peroxide solution shortly before use. The mixture is allowed to act on 100% greyed natural hair at 40° C. for 30 minutes. Thereafter, the colouring composition is rinsed out, and the hair is subsequently shampooed and dried. The hair has been given an intensive dark smoke grey shade.

Hair colouring compositions according to the invention can also be prepared with the following compounds analogously to the descriptions of Examples 4 to 9:

| Example | -2,3-dihydroperimidine | Melting point (°C.) |
|---|---|---|
| 10 | 2-methyl | 70–72 |
| 11 | 2-trichloromethyl | 85–87 |
| 12 | 2-ethyl | 77–79 |
| 13 | 2-diethoxymethyl | 65–66 |
| 14 | 2-propyl | 78–80 |
| 15 | 2-hexyl | 57–58 |
| 16 | 1-phenyl | 97–99 |
| 17 | 1-phenyl-2-methyl | >200 |
| 18 | 2-(3',4'-methylenedioxyphenyl) | 155–157 |
| 19 | 2-(2'-hydroxy-3'-methoxyphenyl) | 187–189 |
| 20 | 2-(2'-hydroxyphenyl) | 196–198 |
| 21 | 4-chloro-2,2-dimethyl | 108–110 |
| 22 | 1-methyl, hydrosulphate | >200 |
| 23 | 1,3-dimethyl | 145–149 |
| 24 | 1-(2,3-dihydroperimidin-1-yl)-ethanol | 80–83 |
| 25 | 1(2,3-dihydroperimidin-1-yl)-2-propanol | 74–75 |
| 26 | 4,6-dichloro-1,3-dimethyl | 122–124 |
| 27 | 2,2-dimethyl | 115–117 |
| 28 | 2,2-H | 75–77 |

We claim:

1. Hair Coloring composition comprising a coupler substance and a developer substance which form an oxidation dyestuff, and which are present in amounts which result in a tintorially effective amount of hair color, wherein said coupler comprises a compound of the formula I

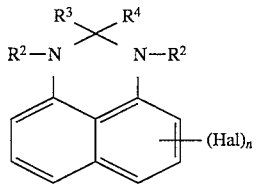

wherein $R^1$ and $R^2$ independently of one another are hydrogen, $(C_1-C_4)$-alkyl, hydroxy-$(C_1-C_3)$-alkyl, 2,3-dihydroxypropyl, 2-hydroxy-3-$(C_1-C_4)$-alkoxypropyl, phenyl or phenyl substituted by 1, 2, or 3 identical or different substituents selected from the group consisting of hydroxy, $(C_1-C_4)$ alkyl, fluorine, chlorine and bromine, or the methylenedioxy radical which simultaneously replaces the atoms of the phenyl radical, $R^3$ and $R^4$ independently of one another are hydrogen trichloromethyl, $(C_1-C_6)$-alkyl, di-$(C_1-C_2)$-alkoxymethyl, hydroxy-$(C_1-C_4)$ alkyl, phenyl or phenyl substituted by 1, 2, or 3 identical or different substituents selected from the group consisting of hydroxy, $(C_1-C_4)$ alkyl, fluorine, chlorine and bromine, or the methylenedioxy radical which simultaneously replaces the atoms of the phenyl radical, Hal is fluorine, chlorine or bromine and n is 0, 1 or 2.

2. The hair coloring composition according to claim 1, wherein the compound of the formula I is present in amounts from about 0.01 to about 5% by weight, based on the total weight of the composition.

3. The hair coloring composition according to claim 1, wherein the compound of the formula I is present in amounts from about 0.1 to about 3% by weight, based on the total weight of the composition.

4. The hair coloring composition according to claim 1, wherein the developer substance is present in amounts from about 0.01 to about 5% by weight, based on the total weight of the composition.

5. The hair coloring composition according to claim 3, wherein the developer substance is present in amounts from about 0.01 to about 5% by weight, based on the total weight of he composition.

6. The hair coloring composition according to claim 1, wherein the developer substance is present in amounts from about 0.1 to about 3% by weight, based on the total weight of the composition.

7. The hair coloring Composition according to claim 5, wherein the developer substance is present in amounts from about 0.1 to about 3% by weight, based on the total weight of the composition.

8. The hair coloring composition according to claim 1, which further comprises other additional color components.

9. The hair coloring composition according to claim 7, which further comprises other additional color components.

10. The hair coloring composition according to claim 1, wherein said hair coloring composition is present in the form of a cosmetic formulation.

11. The hair coloring composition as claimed in claim 1, wherein said developers are 1,4-diaminobenzene, 2,5-diaminotoluene, 2,5-diaminobenzyl alcohol, 4-aminophenol, 4-amino-3-methylphenol, 2,5-diaminopyridine, tetraaminopyrimidine and physiologically tolerated salts thereof.

12. The hair coloring composition as claimed in claim 9, wherein said developers are 1,4-diaminobenzene, 2,5-diaminotoluene, 2,5-diaminobenzyl alcohol, 4-aminophenol, 4-amino-3-methylphenol, 2,5-diaminopyridine, tetraaminopyrimidine and physiologically tolerated salts thereof.

* * * * *